United States Patent
Fleischmann (12)

(10) Patent No.: US 6,359,189 B1
(45) Date of Patent: Mar. 19, 2002

(54) PROCESS AND BANDAGE FOR TREATMENT OF WOUNDS

(76) Inventor: Wilhelm Fleischmann, Wieselweg 26, D-74321 Bietigheim-Bissingen (DE)

( * ) Notice: Subject to any disclaimer, the term of this patent is extended or adjusted under 35 U.S.C. 154(b) by 0 days.

(21) Appl. No.: 09/484,116

(22) Filed: Jan. 14, 2000

(30) Foreign Application Priority Data

Jan. 14, 1999 (DE) .......................................... 199 01 134

(51) Int. Cl.[7] ................................................. A61F 13/00
(52) U.S. Cl. ............................. 602/41; 602/42; 602/43; 602/44; 602/45; 602/46; 602/47
(58) Field of Search ............................ 602/41, 42, 47, 602/43–46

(56) References Cited

U.S. PATENT DOCUMENTS

| 4,668,228 A | 5/1987 | Bolton et al. |
| 4,904,469 A | 2/1990 | Petereit et al. |

FOREIGN PATENT DOCUMENTS

| DE | 31 39 089 A1 | 4/1983 | ............ A61K/9/70 |
| EP | 0 194 647 B1 | 9/1986 | ............ A61L/15/06 |
| EP | 0 236 610 A | 9/1987 | ............ A61L/15/03 |

OTHER PUBLICATIONS

Sherman R A: "A new dressing design for use with maggot therapy", Plastic and Reconstructive Surgery, Bdg. 100, 1997, pp. 451–456.

Prete P E: "Growth effects of Phaenicia Sericata larva extracts on fibroblasts: Mechanism for wound healing by maggot therapy", Life Sciences, Bd. 60, Nr. 8, 1997, pp. 505–510.

Fine A et al: "Maggot Therapy. Technique and Clinical Application", Journal of Bone and Joint Surgery, Bd. 16A, 1934, pp. 572–582.

Primary Examiner—Michael A. Brown
Assistant Examiner—Lalita M. Hamilton
(74) Attorney, Agent, or Firm—Pendorf & Cutliff

(57) ABSTRACT

A bandage for treatment of wounds is described, including a wound overlay, which contains the secretion of fly larvae. The wound overlay can be a single pouch or may be subdivided into chambers, which enclose living fly larvae. It is likewise possible to soak or permeate the wound overlay with the secretion of fly larvae.

9 Claims, 1 Drawing Sheet

PROCESS AND BANDAGE FOR TREATMENT OF WOUNDS

BACKGROUND OF THE INVENTION

1. Field of the Invention

The invention concerns a process and a bandage for treatment of wounds.

For treatment of wound infections and wounds which contain dead tissue, for example, for treatment of the diabetic gangrene, fly larvae are employed, in particular larvae of the fly genus Lucilia (bluebottle flies) and in particular *Lucilia scricata*. The fly larvae (maggots) are employed for a specific amount of time, for example three days, in the wound in need of therapy. It has been shown that the maggots in this time remove necrotic tissue in the wound (biodebridement), eliminate bacterial infections and stimulate healing of the wound.

2. Description of the Related Art

In the method for treatment with surgical maggots employed until now, after cleansing of the wound the edge or rim of the wound is first covered with an adhesive strip. The maggots are applied to a fine mesh net, which is then inverted and adhered to the adhesive strips, such that the maggots are situated between the net and the wound surface. The net serves as an air-permeable cage, which restrains the maggots in the wound. After the effective time of approximately three days, the net is pulled off and the maggots are removed from the wound.

In this method, various problems can occur. The adhesive bond between the net and the wound edge is not absolutely reliable. If the adhesive edge comes loose, it is not possible to prevent escape of maggots, which can then pupate so that bottle flies develop. The removal of the maggots from the wound after conclusion of the treatment is time-consuming and, in particular for the patients, is not aesthetic. Further, in larger wounds it cannot be guaranteed that the maggots are active in particular there where the strongest therapeutic effect is to be targeted.

SUMMARY OF THE INVENTION

The present invention is concerned with a task of providing a process and a bandage for treatment of wounds, which overcome or reduce the above-mentioned disadvantages associated with the known treatment with surgical maggots.

The invention is based upon the recognition that the therapeutic effect of the maggots on the wound is in particular attributable to the secretions secreted by the maggots. These secretions, in particular the digestive secretions, liquefy necrotic tissue so that it can be taken up by the maggots as nutrient. The secreted fluid has a strongly anti-bacterial effect and promotes wound healing.

The fundamental concept of the invention is based on the idea that the maggots are not to be freely released into the wound, but rather a wound overlay or applique is to be to employed, which contains the secretion of fly larvae important for the therapeutic effect. The wound overlay can be strategically placed there where the secretion is desired to have a therapeutic effect. In this manner it can be ensured that even in larger wounds the entire wound surface can come in contact with the secretion in an even manner. Likewise, specific areas of the wound can be targeted for treatment with a higher dose and concentration of the secretion.

The wound overlay can be applied with good contact with the wound surface. For this, one can also employ in certain cases a core or insert, which urges the wound overlay to lie against the wound surface. The good surface contact between the wound overlay and the wound surface ensures that the secretion is effective in the entire area of the wound surface. The wound overlay can, after conclusion of the active period, be removed from the wound in a simple and problem-free manner without leaving residues.

In a preferred embodiment, a pouch of a fine-mesh net-like material, preferably a textile material, containing fly larvae is included in the wound overlay. One or more pouches, which contain the maggots, are introduced into the wound. The maggots contained in the pouch have no chance of escape or to migrate to other wound areas. Thereby, it is not only ensured that the maggots do not escape from the wound, but rather it is in particular also insured, that the maggots exercise their therapeutic effect in that wound area where the pouch is applied. In this way it is possible to produce a targeted enhanced or strengthened therapeutic effect in certain wound areas. Likewise, it can be ensured, by the application of multiple small-area pouches, or by the application of one large surface area pouch which is subdivided into smaller enclosed chambers, that the maggots were distributed evenly over the entire wound surface and that they do not collect in an undesired manner in certain wound areas, in which for example the therapeutic effect is less necessary. Finally, by the enclosure of the maggots in a pouch, a rapid, simple and reliable removal of the maggots from the wound is possible. Since the patient does not see the maggots contained in the pouch, the aesthetic and psychological problems of treatment with surgical maggots is substantially reduced.

The material, of which the pouches to be produced, is so finely meshed, that the maggots are reliably enclosed in the pouch. The mesh width of the material, that is, its pore size, is so dimensioned, that an unimpeded fluid exchange of the digestive secretions of the maggots and the dissolved and liquefied necrotic tissue is possible. Further, the textile material of the pouch is sufficiently air permeable to ensure the survival of the maggots.

The fly larvae bred in sterile conditions are introduced into the pouch. It is also possible to introduce fly eggs into the pouches, so that the maggots emerge in the pouch. In order to keep the maggots alive until introduction into the wound, it is possible or necessary, for example, to introduce a maggot specific nutrient media together with the maggots, or to impregnate the pouch therewith. Since the maggots only sustain themselves with dead tissue, such a supplementation of nutrient media can also be important in the case that the wound area, in which the pouch is applied, does not sufficiently contain necrotic tissue.

For the practical application of the wound overlay, it can be of advantage to provide large surface area pouches which can, for use, be cut to size to correspond to the wound. For this, the pouch can be subdivided by suitable means, for example by plastic clamps or adhesive material, so that a separation is possible and after the separation, the partial pouch is closed at the line of separation. It can also be of advantage, when a large surface area wound overlay is provided, for example, in sheets, which is subdivided into small closed chambers, each of which respectively contain a few maggots. This wound overlay can, on the basis of the confinement in chambers, be very simply cut to the required shape. The subdivision into chambers ensures that the maggots are maintained evenly distributed over the entire surface area of the wound overlay and evenly dispensed their secretion.

In the place of pouches, in which living maggots are enclosed, it is also possible to employ a wound overlay which contains no living maggots but instead is permeated with the secretion of maggots. For this, maggots are bred in vitro and fed necroticed tissue, so that they form and release secretion. This secretion is then received and stored in a wound overlay. After removal of the maggots, the wound overlay impregnated with secretion can be applied to the wound. Such a wound overlay without living fly larvae is particularly suitable for such applications, in which in particular the anti-bacterial and healing promoting effect of the secretion is desired. However, it is usually also necessary to remove necrotized tissue from the wound, and in this case the wound overlay with enclosed maggots is to be preferred.

Particularly in the case of large and deep wounds, in order to apply the wound overlay to the wound surface with good contact, it is preferable when the bandage supplementally includes a core or enclosure, which is applied upon the wound overlay and secured by an outer wound covering. The wound covering presses the core or insert against the wound overlay, whereby again the wound overlay is brought into good contact with the wound surface. The core or insert is preferably comprised of an open-pore material, in particular a foam plastic. As outer wound covering a plastic foil is preferably employed, which is applied over the wound and adhered to the wound edges. Such a foil as wound covering has the advantage, that the wound is closed off air-tight, whereby the development of the offensive strong odor of necrotic tissue is prevented.

If the insert is comprised of an open-pore foam material, then the insert can take up and store surplus wound secretion. In the application of pouches with living maggots, the open-pore insert also serves as storage area for air and moisture, which is necessary for the survival of the maggots when the wound is closed over with an air-tight foil.

If living maggots are employed, then it is advantageous when the air-tight covering of the wound is combined with a ventilation system. By means of such a ventilation system sufficient air can be introduced under the foil and into the open-pore insert, in order to ensure the survival of the maggots. In order to prevent the escape through the ventilation system of the odors evolved in the wound, the ventilation system is preferably closeable or sealable. When air is being supplied below the air-tight covering, the ventilation system is opened and the flow-through of air is carried out through the open porous insert. The emitted odors can, as desired, be captured by an odor filter. Between the individual ventilation phases, the ventilation system can be closed by an air-tight lid.

BRIEF DESCRIPTION OF THE DRAWINGS

In the following the invention will be described in greater detail by reference to the attached drawings. There is shown.

DETAILED DESCRIPTION OF THE INVENTION

Figure 1:
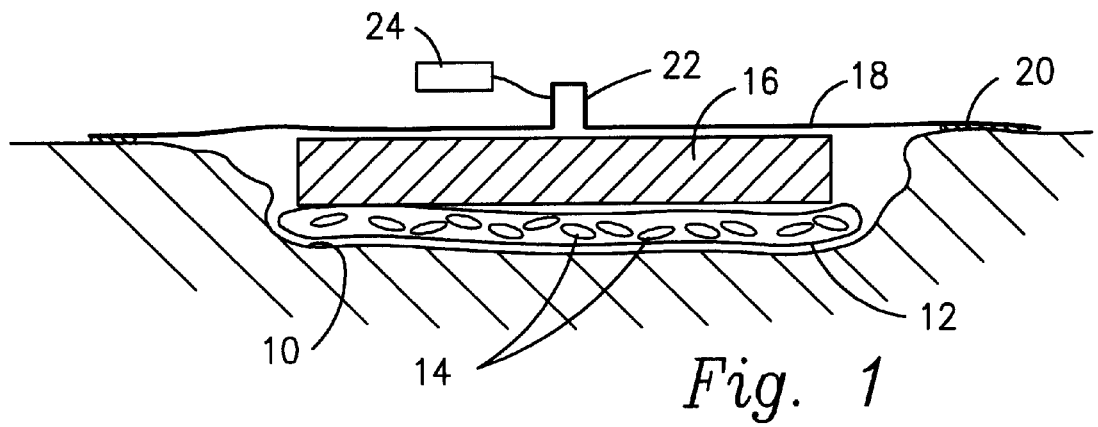
FIG. 1 a vertical section through a wound with bandage.

The pouch 12 comprised of a fine-mesh net-like material is introduced in a wound 10. The sheet-like pouch 12 is closed around its edges. In the pouch 12 there are enclosed sterile-bred living maggots 14 of the fly species *Lucilia sericata*. On the pouch 12 there is applied an insert 16 cut to conform to the wound surface, which insert is comprised of an open-pore foam plastic. The entire wound 10 including the wound overlay formed by the pouch 12 and the open-pore insert 16 is covered over by an air impermeable foil 18, which is securely adhered around the edges of the wound 10 in an air-tight manner using an adhesive substance 20. The foil 18 serving as wound covering includes for ventilation a connector 22, which can be closed off by means of a cap 24 connected to the connector 22 via a flexible flat connector.

For ventilation of the open-pore insert 16 a ventilation system, which may include an odor filter, is connected to the connector 22. Between the individual ventilations, the connector 22 is closed off air tight by means of the cap 24. In a simple manner, the ventilation can also be carried out manually by raising and compressing the foil 18.

Figure 2:
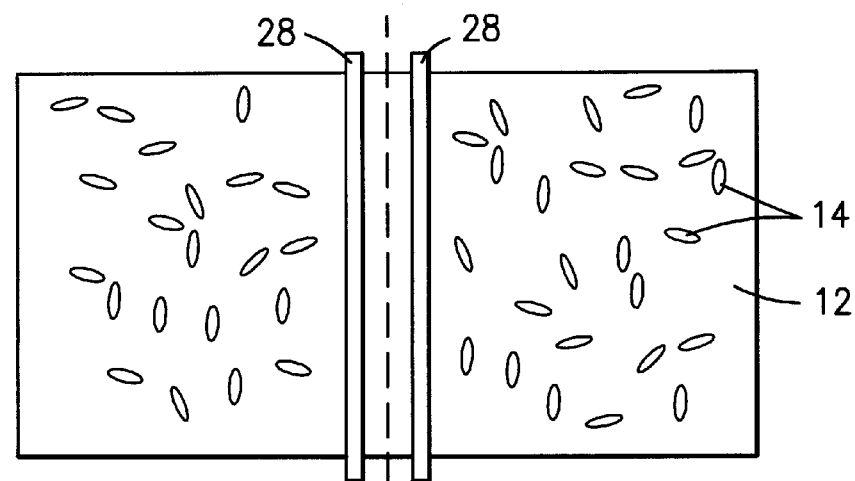
FIG. 2 a fly-larvae enclosing pouch.

Preferably the wound overlay is provided in the form of a large surface area pouch 12. This pouch 12 can as required be subdivided into smaller pouches. As shown in FIG. 2, for this the pouch is closed off on both sides by a desired separation line 26, for which for example plastic clamps 28 can be employed. Likewise an adhering of the two pouch edges is possible. After the closing off of the pouch by the clamps 28 or as the case may be an adhesive, the pouch 12 can be cut through along the separation line 26, so that two closed partial pouches are obtained.

In place of a pouch 12 containing living maggots 14, it is also possible to employ a wound overlay, which is made of a material impregnated with the secretion of fly larvae 14.

Figure 3:
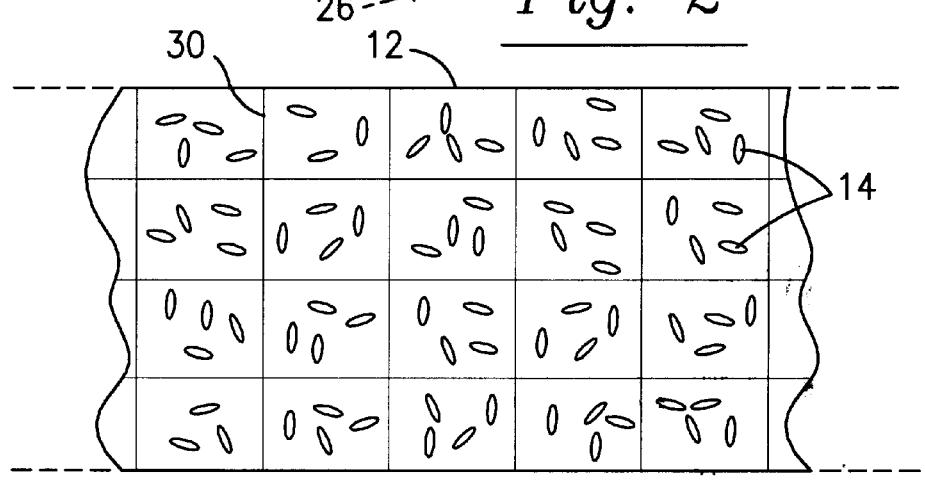
FIG. 3 a pouch subdivided into chambers in a grid-like manner.

In FIG. 3 a further embodiment of the wound overlay is shown. The pouch 12 is comprised of a two-layer sheet of the fine-mesh net-like textile material. Adhesive weld lines or beads 13 connect the sheets running in the longitudinal direction and in transverse direction of the sheet, or in such a manner that the pouch 12 is subdivided into a checkerboard-like grid of closed chambers. Each of these chambers contains a few fly larvae 14. This number can vary, depending on the size of the chamber, from 1–5 or 10 or more fly larvae.

The subdivision of the pouch 12 into individual chambers has the advantage that the fly larvae 14 remain distributed in an even manner over the entire surface area. Further, the subdivision of the pouch 12 into a grid of chambers makes possible in simple manner a cutting or trimming of the wound overlay to correspond to the dimensions of the wound. The wound overlay can be cut in any desired shape, whereby only the maggots 14 contained in the cut-through chambers are lost.

What is claimed is:

1. A bandage for treatment of wounds, comprising:
   living fly larvae, and
   a pouch (12) of a fine-mesh net material enclosing said fly larvae (14),
      wherein said fine-mesh material has a pore size adapted to allow a fluid exchange of secretions of fly larvae and dissolved and necrotic tissue from said wound, and is dimensioned to retain said larvae in said pouch and to separate said fly larvae from said wound, and
      wherein the pouch (12) is subdivided into a plurality of chambers, wherein each chamber contains a number of fly larvae (14).

2. A bandage according to claim 1, wherein the pouch (12) contains a nutrient media for the fly larvae (14).

3. A bandage for treatment of wounds, comprising:
   fly larvae,
   a fine-mesh material having a pore size allowing a fluid exchange of secretions of fly larvae and dissolved and necrotic tissue, and dimensioned to separate fly larvae from said wound, and further including an insert (16) applied upon the wound overlay (12), wherein the insert (16) is comprised of an open-pore foam material.

4. A bandage for treatment of wounds, comprising:

a fine-mesh material having a pore size adapted to allow a fluid exchange of secretions of fly larvae and dissolved and necrotic tissue, and fly larvae, wherein said-fine mesh material is dimensioned to separate fly larvae from said wound, further including a wound cover (18) covering the wound overlay (12) and optionally an insert (16), wherein the wound covering is an air-impermeable foil (18).

5. A bandage according to claim 4, wherein the wound cover (18) includes an adhesive material (20) for adhesion to the wound edge.

6. A bandage according to claim 4, wherein said wound cover (18) is an air impermeable wound covering, and wherein the air impermeable wound covering (18) includes a closeable ventilation access (22, 24).

7. A process for treatment of wounds, comprising:

applying living fly larvae to a wound overlay such that said fly larvae secrete secretions into the wound overlay, removing living fly larvae from the secretion-soaked wound overlay, and applying the soaked wound overlay to the wound, such that said overlay releases fly larvae secretion into the wound.

8. A bandage for treatment of wounds, comprising:

living fly larvae, a pouch (12) of a fine-mesh net material enclosing said fly larvae (14), and wherein said fine-mesh material has a pore size adapted to allow a fluid exchange of secretions of fly larvae and dissolved and necrotic tissue from said wound, and is dimensioned to retain said larvae in said pouch and to separate said fly larvae from said wound, wherein the pouch (12) is impregnated with a nutrient media for the fly larvae.

9. A bandage for treatment of wounds, comprising:

fly larvae, and a fine-mesh material having a pore size adapted to allow a fluid exchange of secretions of fly larvae and dissolved and necrotic tissue, and dimensioned to separate fly larvae from said wound, further including an insert (16) applied upon the wound overlay (12), wherein the insert (16) is comprised of an open-pore foam plastic.

* * * * *